US010729347B1

(12) United States Patent
Schleicher

(10) Patent No.: US 10,729,347 B1
(45) Date of Patent: Aug. 4, 2020

(54) DEVICE WITH LIGHT-PROCESSING COMPONENT COVERED BY LIGHT-PERMEABLE TOUCHABLE ELECTRODE FOR DETECTING BIOLOGIC ACTIVITY

(71) Applicant: Verily Life Sciences LLC, South San Francisco, CA (US)

(72) Inventor: Brett Schleicher, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 241 days.

(21) Appl. No.: 15/884,909

(22) Filed: Jan. 31, 2018

Related U.S. Application Data

(60) Provisional application No. 62/452,538, filed on Jan. 31, 2017.

(51) Int. Cl.
| | | |
|---|---|---|
| *A61B 5/0408* | (2006.01) | |
| *A61B 5/044* | (2006.01) | |
| *A61B 5/00* | (2006.01) | |
| *A61B 5/0492* | (2006.01) | |
| *A61B 5/0476* | (2006.01) | |
| *A61B 5/0404* | (2006.01) | |
| *A61B 5/0205* | (2006.01) | |
| *A61B 5/1455* | (2006.01) | |

(Continued)

(52) U.S. Cl.
CPC .......... *A61B 5/0408* (2013.01); *A61B 5/0205* (2013.01); *A61B 5/044* (2013.01); *A61B 5/0404* (2013.01); *A61B 5/0476* (2013.01); *A61B 5/0492* (2013.01); *A61B 5/14551* (2013.01); *A61B 5/681* (2013.01); *A61B 5/6802* (2013.01); *A61B 5/024* (2013.01); *A61B 5/0533* (2013.01); *A61B 5/6826* (2013.01); *A61B 5/6831* (2013.01); *A61B 5/742* (2013.01)

(58) Field of Classification Search
CPC ... A61B 5/0408; A61B 5/0205; A61B 5/6802; A61B 5/681; A61B 5/6826
USPC ....................................................... 600/508
See application file for complete search history.

(56) References Cited

U.S. PATENT DOCUMENTS

| | | |
|---|---|---|
| 4,412,546 A | 11/1983 | Barthels et al. |
| 5,876,350 A | 3/1999 | Lo et al. |

(Continued)

*Primary Examiner* — Amanda K Hulbert
*Assistant Examiner* — Philip C Edwards
(74) *Attorney, Agent, or Firm* — Kilpatrick Townsend & Stockton LLP

(57) ABSTRACT

A device may include a housing, a light-permeable electrode, a computing device, and a display or other light-processing element. The display or other light-processing element may be positioned at least partly within the housing. The device components may be arranged to permit passage of light through the light-permeable electrode and relative to the light-processing element. The computing device may utilize electrical activity signal information from the light-permeable electrode to determine electrocardiogram (ECG) information or other information about the body of a user of the device. For example, the computing device may cause such ECG information to be projected through the light-permeable electrode by the display or other light-processing device and/or obtain additional information based on light received through the light-permeable electrode by the display or other light-processing device.

35 Claims, 4 Drawing Sheets

(51) Int. Cl.
*A61B 5/024* (2006.01)
*A61B 5/053* (2006.01)

(56) References Cited

U.S. PATENT DOCUMENTS

| | | |
|---|---|---|
| 5,931,764 A | 8/1999 | Freeman et al. |
| 2014/0336516 A1* | 11/2014 | Rizzo ..................... A61B 5/05 600/476 |
| 2016/0089053 A1* | 3/2016 | Lee ..................... A61B 5/0537 600/384 |

\* cited by examiner

US 10,729,347 B1

DEVICE WITH LIGHT-PROCESSING COMPONENT COVERED BY LIGHT-PERMEABLE TOUCHABLE ELECTRODE FOR DETECTING BIOLOGIC ACTIVITY

PRIOR RELATED APPLICATION

This application claims priority to U.S. Provisional Application No. 62/452,538, filed Jan. 31, 2017, entitled "DEVICE WITH LIGHT-PROCESSING COMPONENT COVERED BY LIGHT-PERMEABLE TOUCHABLE ELECTRODE FOR DETECTING BIOLOGIC ACTIVITY", which is hereby incorporated by reference in its entirety herein.

TECHNICAL FIELD

The present disclosure generally relates to devices that detect activity of the human body, and more specifically, but not necessarily limited to, body-worn devices for detecting heart activity of a wearer of the device.

BACKGROUND

Various devices exist for tracking human biologic activity. For example, devices may use any of a variety of inputs to track a person's heart rate, blood oxygenation levels, steps taken in a particular time period, or other metrics. Such devices are often included in a watch or have another form factor that facilitates ease of wearing or use in everyday life.

SUMMARY

Various examples of the present disclosure are directed to a watch or other device with an electrode that is touchable to provide an electrocardiogram or other body activity reading and that is light-permeable or transparent to permit passage of light to and/or from a display or other light-processing component of the device.

In one example, a device can be provided that includes a housing, a strap, a wrist-facing electrode, a light-permeable electrode, a light-receiving sensor, and a light-emitting display. The housing can define an internal space. The strap can be coupled with the housing for securing the housing to a wrist of a first hand of a wearer in a donned state of the strap. The wrist-facing electrode can be coupled with the housing so as to contact the wrist of the first hand of the wearer for obtaining a first electrical activity signal from the wearer in the donned state. The light-permeable electrode can be coupled with the housing in a location that is accessible for touching by a second hand of the wearer for obtaining a second electrical activity signal from the wearer in the donned state. The computing device can be at least partially within the internal space defined by the housing. The computing device can be communicatively coupled with the wrist-facing electrode and the light-permeable electrode. The computing device can include a processor and a non-transitory computer-readable medium including processor-executable instructions to cause the processor to determine electrocardiogram information based at least upon the first electrical activity signal from the wrist-facing electrode and the second electrical activity signal from the light-permeable electrode. The light-receiving sensor can be within the internal space of the housing and aligned with the light-permeable electrode for receiving inwardly directed light through the light-permeable electrode. The light-receiving sensor can be communicatively coupled with the computing device for providing to the computing device information about the inwardly directed light. The light-emitting display can be communicatively coupled with the computing device. The light-emitting display can be located within the internal space of the housing and aligned with the light-permeable electrode for emitting outwardly directed light outward through the light-permeable electrode in response to communication from the computing device.

In another example, a device includes a housing, a light-permeable electrode, a computing device, and a display. The housing can define an internal space. The light-permeable electrode can be coupled with the housing in a location that is accessible for contact with a first portion of a body of a user of the device for obtaining a first electrical activity signal from the first portion of the body of the user. The computing device can be at least partially within the internal space defined by the housing. The computing device can be communicatively coupled with the light-permeable electrode. The computing device can include a processor and a non-transitory computer-readable medium comprising processor-executable instructions to cause the processor to determine information about the body of the user based at least upon the first electrical activity signal from the light-permeable electrode. The display can be at least partially covered by the light-permeable electrode so as to be visible through the light-permeable electrode from outside of the internal space.

In a further example, a device includes a housing, a light-processing element, a light-permeable electrode, and a computing device. The housing can define an internal space. The light-processing element can be at least partially received in the housing. The light-permeable electrode can be at least partially overlaying the light-processing element in an arrangement permitting passage of light relative to the light-processing element through the light-permeable electrode. The light-permeable electrode can be positioned in a location that is accessible for contact with a first portion of a body of a user of the device for obtaining a first electrical activity signal from the first portion of the body of the user. The computing device can be at least partially within the internal space defined by the housing. The computing device can be communicatively coupled with the light-permeable electrode. The computing device can include a processor and a non-transitory computer-readable medium comprising processor-executable instructions to cause the processor to determine information about the body of the user based at least upon the first electrical activity signal from the light-permeable electrode.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
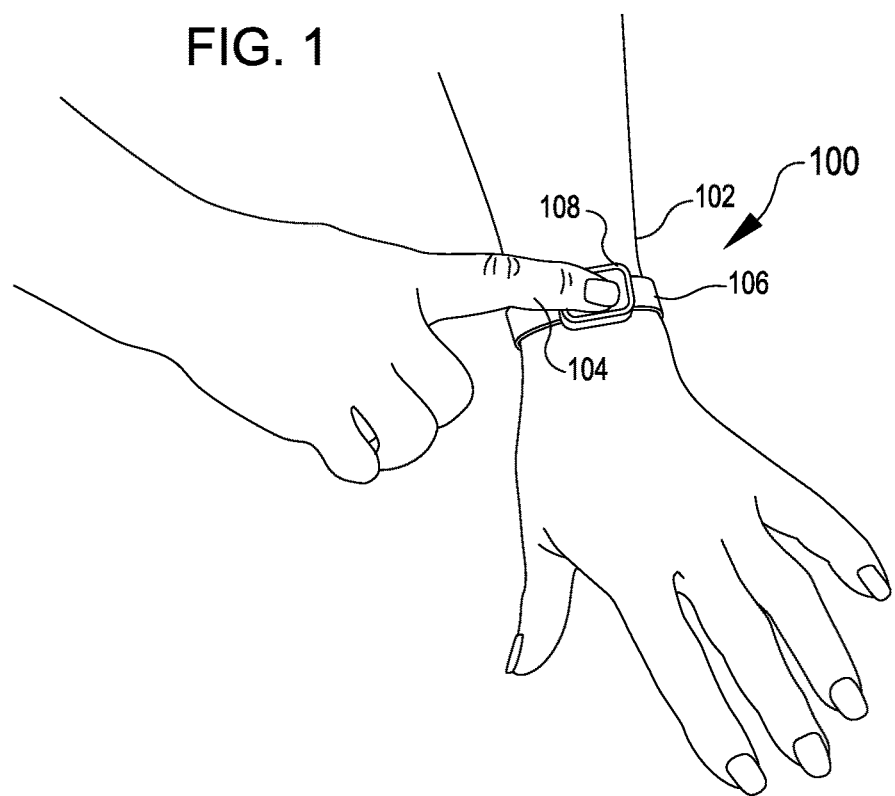
FIG. 1 shows an illustrative example of a device being used for detecting electrocardiogram information of a wearer, according to certain examples of the present disclosure.

In the following description, various embodiments are described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

In an illustrative example, a person may wear a watch with a built-in capacity to obtain and display information about the wearer's heart function. As used herein the term watch is used in an exemplary fashion, as a watch-like wearable device lacking traditional timepiece functions may be used. Thus, whenever a watch is referenced herein, a watch-like device could be referenced as well.

The watch includes a housing with electrodes on top and bottom. A watch strap snuggly holds the housing to one of the person's wrists, specifically, the left wrist in this example. The electrode on the bottom of the housing is thus held in contact with the left wrist by the strap. The housing also includes a display in it for showing the time and other information. The top electrode is transparent and positioned over the display so that the display can be seen through the top electrode. The display optionally shows messages or instructions to the wearer or provides output regarding the collected data. For example, the display may show a fingerprint that is visible through the top electrode so that the wearer knows where to touch the top electrode with the opposite hand (right hand in this case). The display may also provide instructions visible to the wearer through the top electrode to maintain contact for a certain period of time. While the right hand is in contact with the top electrode, a chip or other computing device within the watch receives signals from both the bottom electrode and the top electrode, for example, based on natural electrical changes to the person's skin that occur with each heartbeat. The computing device tracks and compares these signals from the left wrist and from the right hand to generate diagnostic information about the person's heart function. This diagnostic information or output information can then be shown on the display for viewing through the transparent top electrode by the wearer. Additionally or alternatively, the display may provide an indication regarding the quality of the contact or signal obtained. Because the top electrode is transparent in this example, the top electrode does not obscure the viewing area of the display and may permit the display to occupy a larger portion of the top face of the watch than might otherwise be possible if the top electrode were instead opaque and to be arranged alongside (rather than over) the display.

Reference will now be made in detail to implementations of examples as illustrated in the accompanying drawings. Like reference indicators will be used throughout the drawings and the following description to refer to the same or like items.

FIG. 1 shows an illustrative example of a device 100 being used for detecting electrocardiogram information of a wearer. In the example shown in FIG. 1, the device 100 is shown in a donned state on wrist 102 of the wearer's left hand and is also being touched by a finger 104 of the wearer's right hand. A strap 106 and a housing 108 of the device 100 are also identified in FIG. 1, although described in greater detail with reference to FIG. 2.

Figure 2:
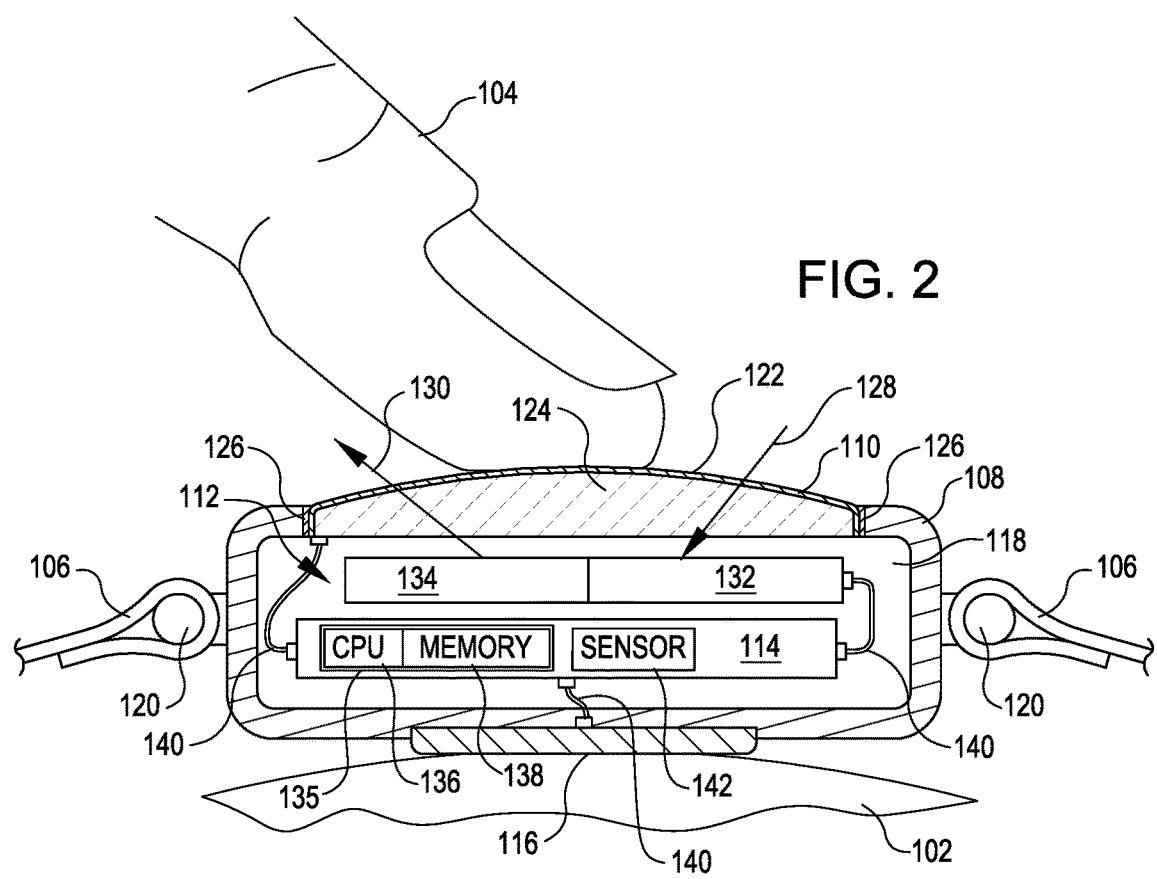
FIG. 2 is a side sectional view showing an illustrative example of components of the device of FIG. 1, according to certain examples of the present disclosure.

FIG. 2 is a side sectional view showing an illustrative example of components of the device 100 of FIG. 1. In the example shown in FIG. 2, the device 100 is shown with the strap 106, the housing 108, a transparent electrode 110, a light-processing element 112, an electronics package 114, and a simple electrode 116 that is arranged as a wrist-facing electrode.

The housing 108 defines an internal space 118 in which various other elements are at least partially located. For example, the electronics package 114 and the light-processing element 112 are shown in FIG. 2 within the internal space 118 of the housing 108. In the arrangement shown, the transparent electrode 110 provides a boundary to the internal space 118 of the housing 108 and at least partially closes off the internal space 118 from an exterior of the housing 108. For example, the light-processing element 112 may be arranged within the internal space 118 of housing 108 so as to be at least partially covered or overlaid by the transparent electrode 110.

The housing 108 may be formed of any suitable material. In some examples, the housing 108 is formed of metal or other electrically conductive material. In some examples, the housing is formed of plastic or other electrically nonconductive material.

The housing 108 is shown attached to the strap 106 by posts 120. However, other attachment structure additionally or alternatively may be used. In some examples, the housing 108 and the strap 106 may be integrally formed as a single part.

The strap 106 is shown in FIG. 2 securing the housing 108 relative to the wrist 102 of the wearer. This securement to the wrist 102 maintains the simple electrode 116 (at the exterior bottom of the housing 108 in FIG. 2) in contact with the wrist 102 of the wearer and maintains the transparent electrode 110 (at the exterior top of the housing 108 in FIG. 2) in a position accessible for touching by the finger 104 of the wearer. Generally, such an arrangement can allow the simple electrode 116 to provide one electrical signal from the wrist 102 of one hand of the wearer and permit the transparent electrode 110 to provide a distinct electrical signal from a finger 104 of an opposite hand of the wearer.

The simple electrode 116 can include any suitable electrically conductive material for obtaining electrical signals from the body of the wearer of the device 100. In some examples, the simple electrode 116 may be opaque. Although the simple electrode 116 is shown in FIG. 2 as a separate component from the housing 108, in some examples, the simple electrode 116 may instead form an integral part of the housing 108, such as in arrangements in which the housing 108 includes electrically conductive material. In some examples, the simple electrode 116 may include or be supplemented by multiple electrodes. For example, an additional reference electrode may be included to provide information that can be utilized to eliminate common 60 hz noise.

The transparent electrode 110 is light-permeable. In some examples, the transparent electrode may be less than 100% transparent or less than 100% clear. For example, the transparent electrode 110 may include some degree of frosting or tinting. In some examples, 100% opaque masking may be present in some areas to direct the user's focus to particular areas of the electrode or serve as decorative features. Generally, the transparent electrode 110 may be sufficiently light-permeable to permit passage of light through the transparent electrode 110 and relative to the light-processing element 112. For example, the transparent electrode 110 may permit passage of inwardly directed light (e.g., as illustrated at 128) from the exterior of the housing 108 through the transparent electrode 110 and into the internal space 118 of the housing 108. As another example, the transparent electrode 110 may permit passage of outwardly directed light (e.g., as illustrated at 130) from the internal space 118 of the housing 108 through the transparent electrode 110 and out to the exterior of the housing 108.

In FIG. 2, the transparent electrode 110 is shown including a base layer 124 topped by a conductive layer 122. The base layer 124 may be formed from a translucent or light-permeable material. Suitable examples include, but are not limited to, glass, sapphire, and plastic. In some examples, the base layer 124 may function as a lens for adapting optical characteristics of light passing through the base layer 124.

In some examples, the conductive layer 122 may be a portion of the base layer 124. For example, the conductive layer 122 may correspond to a portion of the base layer 124 into which conductive elements have been embedded. In some examples, the conductive layer 122 may be a separately formed layer that is joined or applied to the base layer 124. For example, the conductive layer 122 may correspond to a film applied to the base layer 124. In some examples, the conductive layer 122 may be provided in the absence of a base layer 124.

A variety of materials and techniques may be utilized in forming the conductive layer 122. Generally, the conductive layer 122 may be formed by any technique that renders the conductive layer 122 electrically conductive with light-permeable characteristics. As some examples, the conductive layer 122 may correspond to a film including indium tin oxide, transparent gold, aluminum oxide, transparent aluminum, graphene, one or more of other conductive and light-permeable materials, or some combination of any of these options. As further examples, the conductive layer 122 may include embedded conductive micro wires, embedded conductive nano wires, embedded conductive micro wire mesh, embedded nanoparticles, embedded nano-tubes, one or more of other structures of conductive materials combined in a scale and arrangement sufficient to permit passage of light and provide electrical conductivity, or some combination of any of these options.

Insulation 126 may be positioned at an interface between the transparent electrode 110 and the housing 108. For example, in situations in which the housing 108 is electrically conductive, the insulation 126 may prevent electrical conduction between the transparent electrode 110 and the housing 108 that might negatively impact accuracy of readings from the transparent electrode 110 (e.g., due to conduction from the housing 108 having the capacity for altering whatever electrical signal is obtained by the transparent electrode 110). In some examples, the insulation 126 is arranged in a perimeter about the transparent electrode 110. The insulation 126 can correspond to plastic or any other suitable material that is sufficiently electrically non-conductive to prevent conduction between materials physically separated by the insulation 126.

The light-processing element 112 shown in FIG. 2 includes a light-receiving element 132 and a light-emitting element 134, although in some examples the light-processing element 112 may include one without the other.

The light-receiving element 132 receives inwardly directed light 128 through the transparent electrode 110. In one example, the light-receiving element corresponds to a light sensor for obtaining information about ambient light conditions about the device 100.

The light-emitting element 134 projects outwardly directed light 130 through the transparent electrode 110. In some examples, the light-emitting element 134 may produce the outwardly directed light 130. For example, the light-emitting element 134 can correspond to a digital display that produces light in different intensities or colors to vary information shown on the display. In some examples, the light-emitting element 134 may emit outwardly directed light 130 as a reflection without actively producing the outwardly directed light 130. As one example, the light-emitting element 134 may be an analog watch face that reflects light without producing the light. As another example, the light-emitting element 134 can correspond to an e-ink display or other display that alters surface characteristics of the display so that light will reflect differently off of the surface to alter information shown on the display.

The electronics package 114 can include a computing device 135 that receives input from elements of the device 100 and provides output to the same or other elements of the device 100. The computing device 135 in FIG. 2 includes a processor 136 and memory 138. The processor 136 may be implemented as appropriate in hardware, computer-executable instructions, firmware, or combinations thereof. The memory 138 may include any suitable form of non-transitory computer-readable medium. The memory 138 can include instructions which are generally executed by the processor 136 for implementing the features disclosed herein. Computer-executable instruction or firmware implementations of the processor 136 may include computer-executable or machine-executable instructions written in any suitable programming language to perform the various functions described. The memory 138 in various examples can store information from input provided to the computing device 135 from other elements of the device 100, which may allow the information to be later accessed and/or further processed.

In some examples, the electronics package 114 includes one or more sensors 142. The sensor 142 may provide additional information to the computing device 135, for example, to facilitate monitoring of body activity by the wearer of the device 100. In some examples, the sensor 142 may include an accelerometer, global positioning system (GPS) device, or other sensor capable of providing information about location or movement of the device 100 and consequently location or movement of the wearer.

The computing device 135 is shown in FIG. 2 communicatively coupled via wired connections 140 with the transparent electrode 110, with the light-processing element 112, and with the simple electrode 116. For ease of viewing, FIG. 2 does not show wires connecting the light-emitting element 134 to the computing device 135 through the intervening structure of the light-receiving element 132 and wires connecting the sensor 142 to the computing device 135. The device 100, however, is not limited to the exact wiring arrangement shown in FIG. 2 for communications between elements. Rather, the device 100 may include any wired connection, wireless connection, or any other suitable communication link by which elements may communicate with each other individually or in combination. As one example, the device 100 may feature an arrangement in which all or part of the computing device 135 is located remote from the housing 108 (e.g., in a paired device or otherwise outside of housing 108) and communicatively coupled via wireless or other suitable connections to permit functions described herein relative to the computing device 135.

In an illustrative example of the device 100 in operation, the computing device 135 receives information via the simple electrode 116 about an electrical signal detected from the wearer's wrist 102. The computing device 135 also receives information via the transparent electrode 110 about a separate electrical signal detected from the wearer's finger 104 of the other hand. Based on the input from the transparent electrode 110 and the simple electrode 116, the computing device 135 determines electrocardiogram (ECG) information about the wearer's heart function. For example, the computing device 135 may use these distinct electrical signals to determine ECG information that includes a vector with direction and magnitude information that can indicate that the wearer's heartbeat is within a particular stage of a heartbeat cycle and how the heart is functioning within that stage. The computing device 135 may store the generated ECG information in the memory 138 to be later accessed and/or further processed.

Continuing with this illustrative example, the computing device 135 may communicate with the light-processing element 112 to cause the light-emitting element 134 to convey the ECG information in outwardly directed light 130 through the transparent electrode 110. For example, the computing device 135 may provide output that causes a charted heartbeat to be shown by the light-emitting element 134, such as by producing light that shows the charted heartbeat or by adjusting an e-ink digital display so that light reflecting from the display will show the charted heartbeat. The light-emitting element 134 may additionally or alternatively cause the outwardly directed light 130 to convey pulse numbers, historical comparisons, prompts to the wearer to seek medical attention or take other action, or other variations of the ECG information.

In some examples, the computing device 135 may utilize information from other elements of the device 100 to determine output to provide to the light-processing element 112. For example, the computing device 135 may use input from the light-receiving element 132 to determine an ambient light level and then adjust the output provided to the light-emitting element 134 to cause the outwardly directed light 130 to be brighter or dimmer to be more suitable for the light conditions present about the device 100. As another example, the computing device 135 may communicate with the light-emitting element 134 to cause the outwardly directed light 130 to convey information about steps taken by the wearer or some other body activity measurement determined by the computing device 135 based on information from the sensor 142. As a further example, the outwardly directed light 130 may convey time (e.g., a representation of an analog watch face or a representation with digital numbers) or other information determined by the computing device 135.

The computing device 135 additionally or alternatively may perform the necessary calculations, analysis algorithms etc. to determine relevant clinical markers such as r-r interval, qrs duration, mean electrical axis, etc. In some examples, raw data may be stored for analysis by another device or transmitted for analysis. Examples of possible transmission options include but are not limited to transmission through a terminal usb, charging dongle, etc. In some examples, the computing device 135 may receive information from an external device to prompt the user to take action (e.g., to capture an ECG reading) and such prompts may be provided through the display or the light-emitting element 134 and/or transparent electrode 110. Moreover the electronics package 114 may include radios, telemetry (e.g., WIFI, Bluetooth, Bluetooth Low Energy (BLE), cellular), or other communication components to allow the device 100 to communicate to another external device like a smartphone, personal computer, connectivity bridge, etc. to facilitate sending and/or receiving information.

Figure 3:
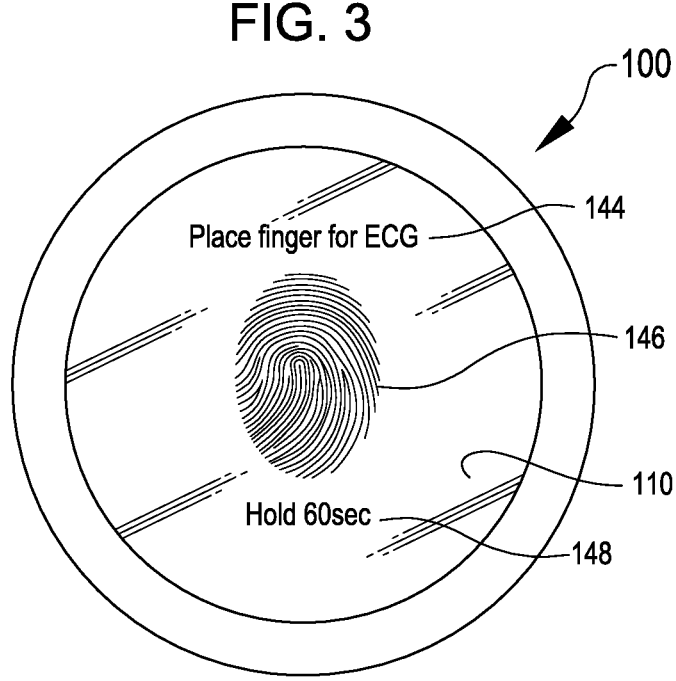
FIG. 3 shows an illustrative example of instructions that may be displayed, according to certain examples of the present disclosure.

In some examples, the computing device 135 may provide prompts to the wearer for use of the device 100. The prompts may be conveyed by outwardly directed light 130 and accordingly visible through the transparent electrode 110. In some examples, the prompts may include information about a timing, location, and/or duration requested for touching of the transparent electrode 110 by the finger 104 of the second hand of the wearer for facilitating obtaining the corresponding electrical activity signal. One example is shown in FIG. 3, in which the device 100 is shown displaying a first prompt 144 for requesting a timing of establishing contact (e.g., to begin immediately), a second prompt 146 regarding a location requested for the contact (e.g., a fingerprint icon to cue the wearer of the location to touch), and a third prompt 148 regarding a duration for maintaining the contact (e.g., perhaps for a period of time sufficiently long for the computing device 135 to be able to obtain sufficient input to provide meaningful output).

Figure 4:
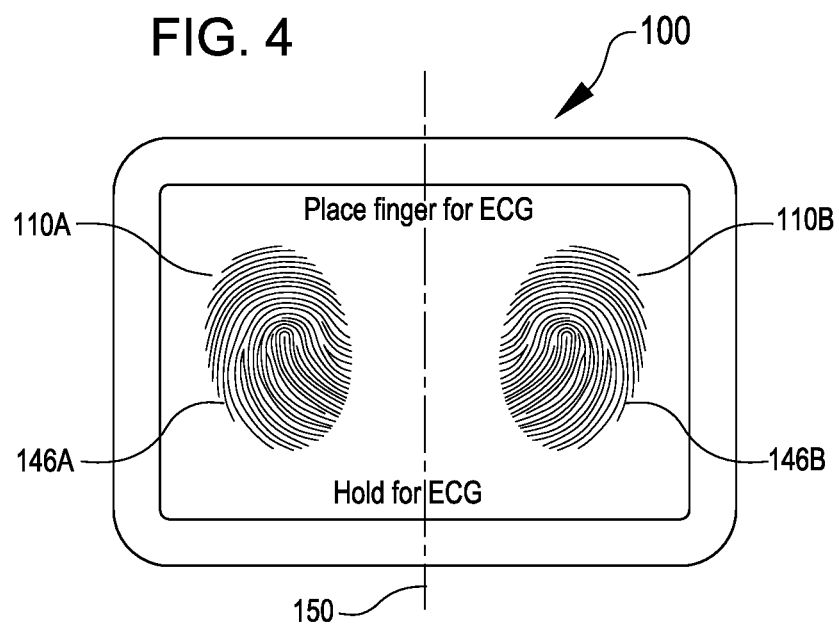
FIG. 4 shows another illustrative example of instructions that may be displayed, according to certain examples of the present disclosure.

FIG. 4 shows an example in which the device 100 is displaying separate location prompts 146A and 146B respectively for different fingers of the wearer's hand. The separate location prompts 146A and 146B may help a user properly align different fingers over separate transparent electrode portions 110A and 110B so that separate signals can be obtained, for example, to reduce noise or otherwise improve accuracy of the ECG information generated by the computing device 135. In some examples, the separate transparent electrode portions 110A and 110B may correspond to separate transparent electrodes 110 (e.g., separated by insulation material that is positioned along a reference line 150 but not readily visible to the viewer), which may be separately communicatively coupled with the computing device 135 to provide distinct electrical signals. In some examples, the separate transparent electrode portions 110A and 110B may be portions of a single subdivided transparent electrode 110. For example, the single transparent electrode 110 may include wires, tubes, or other conductive elements that are sufficiently distinguishable from one another that the computing device 135 can differentiate between signals received from different areas of the single transparent electrode 110.

Figure 5:
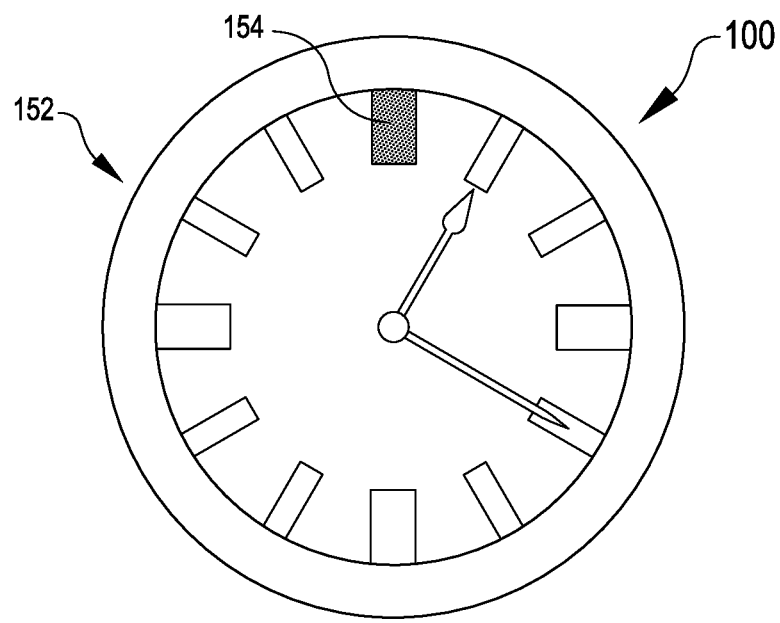
FIG. 5 shows an illustrative example of another display that may be utilized, according to certain examples of the present disclosure.

FIG. 5 illustrates an alternative display option that the device 100 may utilize in some examples. The display shown in FIG. 5 is a display corresponding to a watch face 152 (e.g., of an analog watch). The watch face 152 shown includes a non-transparent electrode 154, which may supplement or substitute for the transparent electrode 110 on the top side of the device 100 for obtaining ECG signals. The non-transparent electrode 154 is shown accessible from an exterior surface and incorporated, for example, into the 12 o'clock hatch mark in the analog watch face 152. In this way, the non-transparent electrode 154 does not take up any space on the watch face 152 that is not already occupied by functional and/or aesthetic visible markings on the watch face 152. In some examples, the non-transparent electrode 154 may additionally or alternatively be positioned other than in the 12 o'clock hatch mark, such as in some other arrangement in which the non-transparent electrode 154 is sized and arranged to avoid occupying any of the watch face that is unoccupied by functional and/or aesthetic visible markings of the watch face 152.

Other variations of the device 100 are possible. For example, although the description above primarily refers to the device 100 being used to provide electrical signals for use in determining ECG information, the device 100 may additionally or alternatively be utilized to obtain other relevant electrical signals. For example, the device 100 may be brought into contact with one or more relevant parts of the body for use in various forms of electrodiagnosis. Electrodiagnosis may include passively recording the electrical activity of body parts (e.g., natural electrophysiology) or measuring response to external electrical stimuli (e.g., evoked potentials). Some more prevalent forms of electrodiagnosis for gauging body part function include electrocardiography (ECG) for the heart; electroencephalography (EEG) for the brain or other central nervous system parts; electromyography (EMG) for muscles or other peripheral nervous system parts, and electrogastrogram (EGG) for the stomach and/or intestinal muscles. Furthermore, the device 100 in various examples may be utilized to obtain electrical signals for gauging skin conductance response (also known as the electrodermal response or galvanic skin response), from which physiological activity may be monitored based on the phenomenon of skin momentarily becoming a better conductor of electricity when either external or internal stimuli are experienced.

Moreover, the device 100 is not limited to arrangements in which a top electrode is a transparent electrode 110 and a bottom electrode is a simple electrode 116 as shown in FIG. 2. The device 100 may include any suitable number of transparent electrodes 110 in any appropriate arrangement, regardless of relative placement of any other transparent electrodes 110 or simple electrodes 116 included on a front, back, top, bottom, or lateral side of the device 100.

Figure 6:
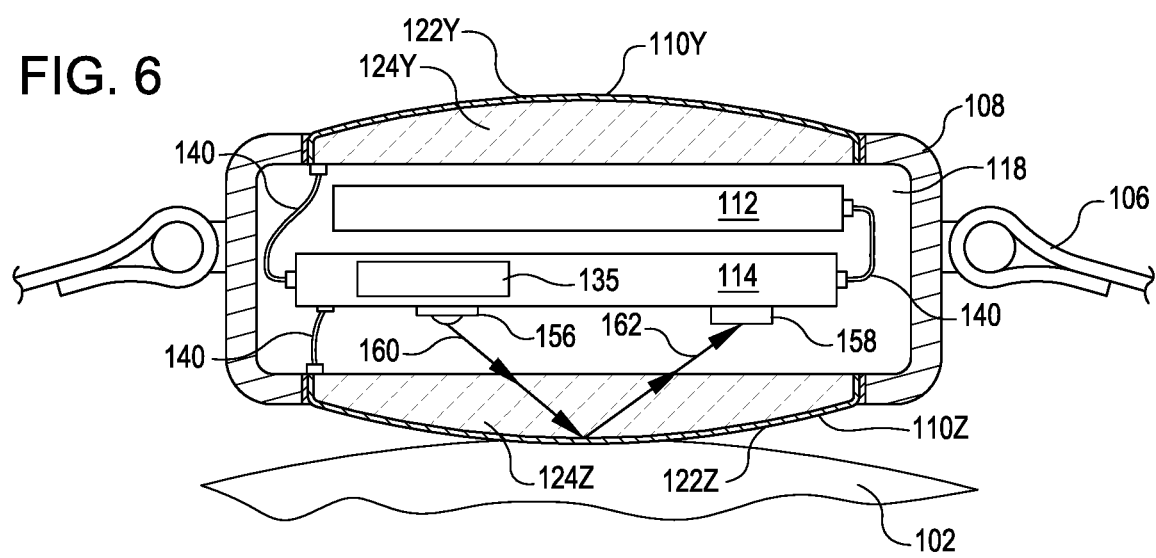
FIG. 6 is a side sectional view showing another illustrative example of device components, according to certain examples of the present disclosure.

FIG. 6 shows one example of another possible arrangement of components in the device 100. The device 100 as shown in FIG. 6 includes many of the same elements as shown in FIG. 2, and as such, description of those elements is not here repeated. The device as shown in FIG. 6 differs from that shown in FIG. 2 in that the simple electrode 116 from FIG. 2 has been replaced with a second transparent electrode 110Z. For the sake of clarity, the respective suffixes "Y" and "Z" are used in FIG. 6 to distinguish between the first transparent electrode 110Y at the top of the housing 108 and the second transparent electrode 110Z at the bottom of the housing 108, although each of these may be examples of the transparent electrode 110 shown in FIG. 2.

In some examples, the first transparent electrode 110Y and the second transparent electrode 110Z may be copies or replicas of one another. In other examples, the first transparent electrode 110Y and the second transparent electrode 110Z may differ from one another in size, shape, or other construction details. For example, if the first transparent electrode 110Y is constructed as described above with respect to FIG. 4 with separate transparent electrode portions 110A and 110B for obtaining separate electrical signals from multiple fingers 104 of the wearer, it may be more cost effective to construct the second transparent electrode 110Z without distinguishable separate transparent electrode portions 110A and 110B since the second transparent electrode 110Z is less likely to utilize such functionality if only being used for obtaining a generalized electrical signal from the wrist 102.

The device 100 is also shown in FIG. 6 with a light source 156 and a light-receptor 158. The computing device 135 may communicate with the light source 156 to cause the light source 156 to project light. The light source 156 may project light at a known frequency, intensity, or other characteristic outwardly (e.g., as illustrated at 160) through the second transparent electrode 110Z, for example, toward the wrist 102 of the wearer. The projected light may reflect from the wrist 102 (or other targeted body part) of the wearer and reflect (e.g., with a modified frequency, intensity, or other characteristic) back through the second transparent electrode 110Z (e.g., as illustrated at 162). The reflected light 162 may be detected by the light-receptor 158, which may provide corresponding information to the computing device 135. The computing device 135 may determine a difference between the projected light 160 and the reflected light 162 to determine characteristics of the wrist 102 or other target body part. For example, the light source 156 and light-receptor 158 may correspond to components of a photoplethysmogram (PPG) device that are commercially available for obtaining information such as pulse, oxygenation levels, or blood flow levels.

In some examples, the light-receptor 158 may be utilized with or without a corresponding light source 156. For example, the light-receptor 158 may correspond to a camera or other component capable (e.g., perhaps with the aid of illumination from the light source 156 if present) of observing the skin or another surface of the wrist 102 or other target body part. The computing device 135 may process the information from the light-receptor 158 to generate other body activity information. For example, the computing device 135 may compare image information from the light-receptor 158 to earlier image information from the light-receptor 158 to determine whether or not skin has become irritated. As another example, the computing device may compare information from the light-receptor 158 against a database or other source of information about relevant criteria to determine if the target body part is showing signs of a particular kind of irritation or other condition.

Moreover, the light source 156 and light-receptor 158 are not limited to a location on a bottom side of the device 100. In some examples, the light source 156 and light-receptor 158 may respectively be examples of—or substitutes for—the light-emitting element 134 or the light-receiving element 132 discussed by way of example on the top of the device 100 with respect to FIG. 2. For example, whereas the position of the light source 156 and light-receptor 158 shown in FIG. 6 may facilitate use of light traveling through the second transparent electrode 110Z to obtain a pulse determination through PPG techniques relative to the wrist 102, re-arranging the light source 156 and light-receptor 158 to work with light traveling through the first transparent electrode 110Y may allow for a pulse determination to instead be made relative to a finger 104.

Moreover, the device 100 is not limited to arrangements in which all elements are arranged in or on a single housing 108. For example, in some examples, one or more components of the device 100 may be located remotely from the housing 108.

Figure 7:
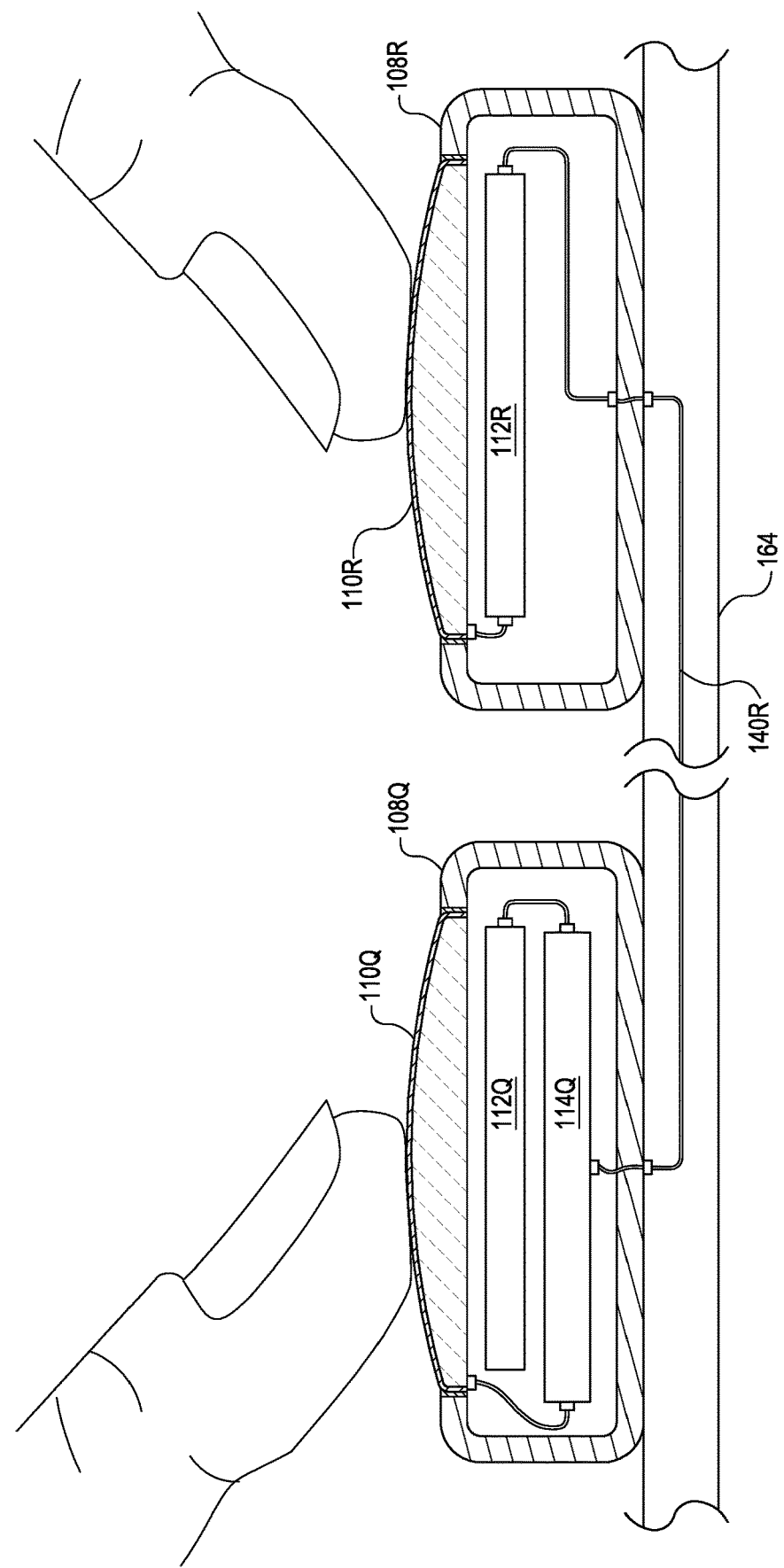
FIG. 7 is a side sectional view showing a further illustrative example of device components, according to certain examples of the present disclosure.

FIG. 7 shows one example of such an arrangement in which some components of the device 100 are located remotely. The device 100 as shown in FIG. 7 includes many of the same elements as shown in FIG. 2, and as such, description of those elements is not here repeated.

The device 100 as shown in FIG. 7 differs from that shown in FIG. 2 in that the simple electrode 116 from FIG. 2 has been eliminated in favor of a second transparent electrode 110R that is remotely located. For the sake of clarity, the suffix "Q" is used in FIG. 7 to denote elements originally introduced with respect to FIG. 2 and the suffix "R" is used to distinguish like additional elements that are introduced in FIG. 7. Although like-numbered elements having different suffixes may be alike, they need not be identical, and in some examples, they may feature variations from one another.

The second transparent electrode 110R is shown remote from the first housing 108Q. A second housing 108R and a second light-processing element 112R are shown associated with the second transparent electrode 110R. Locating the transparent electrode 110R remotely from the first housing 108Q may allow the device 100 to be implemented with a variety of form factors that differ from the watch shown in FIG. 1. In some examples, a remote simple electrode (e.g., similar to the simple electrode 116 of FIG. 2) may be used in place of a remote second transparent electrode 110R. Although the electronics package 114Q is shown in FIG. 7 in the first housing 108Q that has the first transparent electrode 110Q, in some examples, the electronics package 114Q (and/or any other element previously described as includable or present within a housing 108) additionally or alternatively may be partially or completely located outside of the first housing 108Q, such as in or on the second (remote) housing 108R (if present) or elsewhere apart from the first housing 108Q.

In some examples, the device 100 may feature remote components attached by an intervening structure 164. For example, the device 100 may have a form factor of an armband or of a waistbelt, and the intervening structure 164 may correspond to the band or belt leather or other material that forms the main body of the band or belt. The wearer of the belt can optionally touch the first transparent electrode 110Q with one hand and touch the second transparent electrode 110R with the opposite hand to provide electrical signals, e.g., for ECG readings. For example, the wearer might be guided to align the first hand by prompts from the first light-processing element 112Q that are visible through the first transparent electrode 110Q and guided to align the second hand by prompts from the second light-processing element 112R that are visible through the second transparent electrode 110R.

In another example, the intervening structure 164 may correspond to a handheld base, e.g., which may be shaped to allow a user to grip the base and respectively press a thumb down on each of the first transparent electrode 110Q and the second transparent electrode 110R. Thus, considering that this and other form factors may involve a user rather than a wearer of the device, the use of the term "wearer" in preceding description herein should also be understood to be replaceable with the word "user" as relevant.

The intervening structure 164 is shown in FIG. 7 with an internally located wired connection 140R by which the second transparent electrode 110R and the second light-processing element 112R are communicatively coupled with the electronics package 114Q. However, any other suitable communication link may be utilized, including wireless communication. In some examples, using wireless communication between remote elements of the device 100 may facilitate the implementation of various form factors for the device 100. For example, the device 100 may be implemented in any suitable form factor, including, but not limited to, watches, wristbands, bracelets, necklaces, earrings, fobs, dongles, belts, gloves, gauntlets, paired objects held or worn relative to each hand or other body parts, or other sets of two or more intercommunicating components that can be brought into contact with the user.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure. For example, more or fewer steps of the processes described herein may be performed according to the present disclosure. Moreover, other structures may perform one or more steps of the processes described herein.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Some examples in this disclosure may include a processor. A computer-readable medium, such as RAM may be coupled to the processor. The processor can execute computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices, such as programmable logic controllers (PLCs), programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example, computer-readable storage media, that may store instructions that, when executed by the processor, can cause the processor to perform the steps described herein as carried out, or assisted, by a processor. Examples of computer-readable media may include, but are not limited to a memory chip, ROM, RAM, ASIC, or any other medium from which a computer processor can read or write information. The processor, and the processing described, may be in one or more structures, and may be dispersed through one or more structures. The processor may comprise code for carrying out one or more of the methods (or parts of methods) described herein.

Use herein of the word "or" is intended to cover inclusive and exclusive conditions. In other words, A or B or C (or A, B, or C) includes any or all of the following alternative combinations as appropriate for a particular usage: A alone; B alone; C alone; A and B only; A and C only; B and C only; and all three of A and B and C.

That which is claimed is:

1. A device comprising:

a housing defining an internal space;

a strap coupled with the housing for securing the housing to a wrist of a first hand of a wearer in a donned state of the strap;

a wrist-facing electrode coupled with the housing so as to contact the wrist of the first hand of the wearer for obtaining a first electrical activity signal from the wearer in the donned state;

a light-permeable electrode coupled with the housing in a location that is accessible for touching by a second hand of the wearer for obtaining a second electrical activity signal from the wearer in the donned state;

a computing device at least partially within the internal space defined by the housing, the computing device communicatively coupled with the wrist-facing electrode and the light-permeable electrode, the computing device comprising a processor and a non-transitory computer-readable medium comprising processor-executable instructions to cause the processor to determine electrocardiogram information based at least upon the first electrical activity signal from the wrist-facing electrode and the second electrical activity signal from the light-permeable electrode;

a light-receiving sensor within the internal space of the housing and aligned with the light-permeable electrode for receiving inwardly directed light through the light-permeable electrode, the light-receiving sensor communicatively coupled with the computing device for providing to the computing device information about the inwardly directed light; and a light-emitting display communicatively coupled with the computing device, the light-emitting display located within the internal space of the housing and aligned with the light-permeable electrode for emitting outwardly directed light outward through the light-permeable electrode in response to communication from the computing device.

2. The device of claim 1, wherein the outwardly directed light corresponds to light conveying the electrocardiogram information.

3. The device of claim 1, wherein the processor-executable instructions further cause the processor to determine ambient light information based on the information about the inwardly directed light from the light-receiving sensor.

4. The device of claim 1, wherein the processor-executable instructions further cause the processor to determine blood information comprising at least one of pulse information or blood oxygenization information based on the information about the inwardly directed light from the light-receiving sensor wherein the inwardly directed light corresponds to a reflection of light off of skin of the wearer.

5. The device of claim 1, wherein the light-permeable electrode comprises a light-permeable layer and at least one of:

a film comprising indium tin oxide and applied to the light-permeable layer;

a film comprising transparent gold and applied to the light-permeable layer;

a film comprising aluminum oxide or transparent aluminum and applied to the light-permeable layer;

conductive micro wires embedded in the light-permeable layer;

conductive nano-wires embedded in the light-permeable layer;

conductive micro wire mesh embedded in the light-permeable layer;

graphene embedded in the light-permeable layer;

conductive nano-particles embedded in the light-permeable layer; or conductive nano-tubes embedded in the light-permeable layer.

6. A device comprising:

a housing defining an internal space;

a light-permeable electrode coupled with the housing in a location that is accessible for contact with a first portion of a body of a user of the device for obtaining a first electrical activity signal from the first portion of the body of the user;

a computing device at least partially within the internal space defined by the housing, the computing device communicatively coupled with the light-permeable electrode, the computing device comprising a processor and a non-transitory computer-readable medium comprising processor-executable instructions to cause the processor to determine information about the body of the user based at least upon the first electrical activity signal from the light-permeable electrode; and a display at least partially covered by the light-permeable electrode so as to be visible through the light-permeable electrode from outside of the internal space, the display communicatively coupled with the computing device for emitting outwardly directed light through the light-permeable electrode in response to communication from the computing device, the outwardly directed light conveying the information about the body of the user based at least upon the first electrical activity signal from the light permeable electrode.

7. The device of claim 6, wherein the display receives light that travels inwardly through the light-permeable electrode and reflects the light outwardly through the light-permeable electrode without producing a separate source of light.

8. The device of claim 6, wherein the display comprises an analog watch face.

9. The device of claim 8, wherein a hash mark or other decorative feature of the analog watch face comprises a second electrode accessible for contact with a second portion of the body of the user of the device for obtaining a second electrical activity signal usable by the computing device for determining the information about the body of the user.

10. The device of claim 6, wherein the outwardly directed light corresponds to light conveying information about at least one of:

a duration requested for touching of the light-permeable electrode by a hand of the user for facilitating obtaining the first electrical activity signal; or a location requested for touching of the light-permeable electrode by a hand of the user for facilitating obtaining the first electrical activity signal.

11. The device of claim 6, wherein the light-permeable electrode is subdivided into a first portion for touching by a first finger of a hand of the user for obtaining the first electrical activity signal and a second portion for touching by a second finger of the hand of the user for obtaining a second electrical activity signal usable by the computing device for determining the information about the body of the user; and
  wherein the outwardly directed light corresponds to light conveying information about respective locations of the first portion and the second portion requested for respective touching by the first finger and the second finger of the hand of the user for facilitating obtaining the first electrical activity signal and the second electrical activity signal.

12. The device of claim 6, wherein the information about the body of the user comprises at least one of electrocardiogram information, electroencephalogram information, electromyogram information, electrogastrogram information, or galvanic skin response information.

13. The device of claim 6, further comprising:
  a light-receiving sensor at least partially covered by the light-permeable electrode and communicatively coupled with the computing device; and
  a light source at least partially covered by the light-permeable electrode and aligned for projecting light outwardly through the light-permeable electrode for reflection by skin of the user and back inwardly through the light-permeable electrode toward the light-receiving sensor;
  wherein the processor-executable instructions further cause the processor to determine blood information comprising at least one of pulse information or blood oxygenization information based on information from the light-receiving sensor about the light projected from the light source and reflected by the skin.

14. The device of claim 13, wherein the display is communicatively coupled with the computing device for emitting outwardly directed light outward through the light-permeable electrode in response to communication from the computing device, wherein the outwardly directed light corresponds to light conveying the blood information.

15. The device of claim 6, further comprising a second electrode that is accessible for contact with a second portion of the body of the user of the device for obtaining a second electrical activity signal usable by the computing device for determining the information about the body of the user.

16. The device of claim 15, wherein the second electrode is light-permeable and conductive.

17. The device of claim 15, wherein the second electrode is remote from the housing.

18. The device of claim 15, further comprising:
  a strap coupled with the housing for securing the housing to a wrist of a first hand of the user in a donned state of the strap; and
  a light-receiving sensor aligned with the light-permeable electrode for receiving inwardly directed light through the light-permeable electrode, the light-receiving sensor communicatively coupled with the computing device for providing to the computing device information about the inwardly directed light;
  wherein the second electrode is a wrist-facing electrode coupled with the housing so as to contact the wrist of the first hand of the user in the donned state;
  wherein the light-permeable electrode is coupled with the housing in a location that is accessible for touching by a second hand of the user in the donned state;
  wherein the information about the body of the user determined by the processor comprises electrocardiogram information based at least upon the first electrical activity signal and the second electrical activity signal; and
  wherein the display is communicatively coupled with the computing device and aligned with the light-permeable electrode for emitting outwardly directed light outward through the light-permeable electrode in response to communication from the computing device.

19. The device of claim 6, wherein the housing comprises a conductive housing, wherein the device further comprises insulation separating the conductive housing from the light-permeable electrode.

20. The device of claim 6, wherein the light-permeable electrode comprises a light-permeable layer and at least one of:
  a film comprising indium tin oxide and applied to the light-permeable layer;
  a film comprising transparent gold and applied to the light-permeable layer;
  a film comprising aluminum oxide or transparent aluminum and applied to the light-permeable layer;
  conductive micro wires embedded in the light-permeable layer;
  conductive nano-wires embedded in the light-permeable layer;
  conductive micro wire mesh embedded in the light-permeable layer;
  graphene embedded in the light-permeable layer;
  conductive nano-particles embedded in the light-permeable layer;
  conductive nano-tubes embedded in the light-permeable layer; or
  embedded in the light-permeable layer.

21. The device of claim 6, comprising a form factor of a watch, a wristband, a bracelet, a fob, a dongle, a hand-held device, a belt, a necklace, or a lanyard.

22. The device of claim 6, comprising a strap for attaching the device to the body.

23. A device comprising:
  a housing defining an internal space;
  a light-processing element at least partially received in the housing;
  a light-permeable electrode at least partially overlaying the light-processing element in an arrangement permitting passage of light relative to the light-processing element through the light-permeable electrode, the light-permeable electrode positioned in a location that is accessible for contact with a first portion of a body of a user of the device for obtaining a first electrical activity signal from the first portion of the body of the user; and
  a computing device communicatively coupled with the light-permeable electrode, the computing device comprising a processor and a non-transitory computer-readable medium comprising processor-executable instructions to cause the processor to determine information about the body of the user based at least upon the first electrical activity signal from the light-permeable electrode.

24. The device of claim 23, wherein the light-processing element comprises a light-emitting element.

25. The device of claim 24, wherein the light-emitting element comprises a display.

26. The device of claim 24, further comprising a light-receiving sensor, wherein the light-emitting element comprises a light source aligned to project light for reflection by skin of the user inwardly through the light-permeable electrode toward the light-receiving sensor.

27. The device of claim 24, wherein the light source is aligned to project light outwardly through the light-permeable electrode for reflection by the skin of the user.

28. The device of claim 23, wherein the housing comprises a first housing, the device further comprising:
a second housing remote from the first housing and defining a second internal space;
a second light-processing element at least partially received in the second housing; and
a second light-permeable electrode at least partially overlaying the second light-processing element in an arrangement permitting passage of light relative to the second light-processing element through the second light-permeable electrode, the second light-permeable electrode positioned in a location that is accessible for contact with a second portion of the body of the user of the device for obtaining a second electrical activity signal from the second portion of the body of the user usable by the computing device for determining the information about the body of the user.

29. The device of claim 23, wherein the housing comprises a first housing, the device further comprising a second electrode remote from the first housing, the second electrode positioned in a location accessible for contact with a second portion of the body of the user of the device for obtaining a second electrical activity signal from the second portion of the body of the user usable by the computing device for determining the information about the body of the user.

30. The device of claim 23, wherein the light-permeable electrode comprises a light-permeable layer and at least one of:
a film comprising indium tin oxide and applied to the light-permeable layer;
a film comprising transparent gold and applied to the light-permeable layer;
a film comprising aluminum oxide or transparent aluminum and applied to the light-permeable layer;
conductive micro wires embedded in the light-permeable layer;
conductive nano-wires embedded in the light-permeable layer;
conductive micro wire mesh embedded in the light-permeable layer;
graphene embedded in the light-permeable layer;
conductive nano-particles embedded in the light-permeable layer;
conductive nano-tubes embedded in the light-permeable layer; or
embedded in the light-permeable layer.

31. The device of claim 23, further comprising:
a strap coupled with the housing for securing the housing to a wrist of a first hand of the user in a donned state of the strap; and
a second electrode that is accessible for contact with a second portion of the body of the user of the device for obtaining a second electrical activity signal usable by the computing device for determining the information about the body of the user, the second electrode comprising a wrist-facing electrode coupled with the housing so as to contact the wrist of the first hand of the user in the donned state;
wherein the light-permeable electrode is coupled with the housing in a location accessible for touching by a second hand of the user in the donned state;
wherein the information about the body of the user determined by the processor comprises electrocardiogram information based at least upon the first electrical activity signal and the second electrical activity signal;
wherein the light-processing element comprises:
a light-receiving sensor within the internal space of the housing and aligned with the light-permeable electrode for receiving inwardly directed light through the light-permeable electrode, the light-receiving sensor communicatively coupled with the computing device for providing to the computing device information about the inwardly directed light; and
a light-emitting display communicatively coupled with the computing device, the light-emitting display located within the internal space of the housing and aligned with the light-permeable electrode for emitting outwardly directed light outward through the light-permeable electrode in response to communication from the computing device.

32. The device of claim 23, wherein the computing device is located at least partially within the internal space defined by the housing.

33. The device of claim 23, wherein the light-processing element comprises a light-receiving element.

34. The device of claim 23, further comprising a light-emitting display communicatively coupled with the computing device for emitting outwardly directed light outward through the light-permeable electrode in response to communication from the computing device.

35. The device of claim 34, wherein the outwardly directed light corresponds to light conveying the information about the body of the user based at least upon the first electrical activity signal from the light-permeable electrode.

* * * * *